United States Patent
Garcia De Castro Andrews et al.

(10) Patent No.: US 8,506,985 B2
(45) Date of Patent: Aug. 13, 2013

(54) BONE REGENERATION MATERIALS BASED ON COMBINATIONS OF MONETITE AND OTHER BIOACTIVE CALCIUM AND SILICON COMPOUNDS

(75) Inventors: Arcadio Garcia De Castro Andrews, Tres Cantos (ES); Raul Garcia Carrodeguas, Tres Cantos (ES); Sussette Padilla Mondéjar, Tres Cantos (ES); Niuris Acosta Contreras, Tres Cantos (ES)

(73) Assignee: Azurebio, S.L., Madrid (ES)

( * ) Notice: Subject to any disclaimer, the term of this patent is extended or adjusted under 35 U.S.C. 154(b) by 0 days.

(21) Appl. No.: 13/148,147

(22) PCT Filed: Feb. 4, 2010

(86) PCT No.: PCT/EP2010/051386
§ 371 (c)(1),
(2), (4) Date: Sep. 26, 2011

(87) PCT Pub. No.: WO2010/092001
PCT Pub. Date: Aug. 19, 2010

(65) Prior Publication Data
US 2012/0058152 A1    Mar. 8, 2012

(30) Foreign Application Priority Data

Feb. 10, 2009    (WO) .................. PCT/ES2009/070019

(51) Int. Cl.
*A61F 2/02*    (2006.01)
(52) U.S. Cl.
USPC ........................................ 424/426
(58) Field of Classification Search
None
See application file for complete search history.

(56) References Cited

U.S. PATENT DOCUMENTS

| | | | |
|---|---|---|---|
| 6,309,422 B1 | 10/2001 | Farrington et al. | |
| 2002/0084194 A1 | 7/2002 | Redepenning | |
| 2005/0031704 A1 | 2/2005 | Ahn | |
| 2005/0209704 A1 | 9/2005 | Maspero et al. | |
| 2007/0022912 A1 | 2/2007 | Zimmermann | |

FOREIGN PATENT DOCUMENTS

| | | |
|---|---|---|
| WO | WO 98/58602 | 12/1998 |
| WO | WO 2007/000608 A2 | 1/2007 |
| WO | WO 2008/095307 A1 | 8/2008 |
| WO | WO 2009/077210 A1 | 7/2009 |

OTHER PUBLICATIONS

Patel, "Optimising Calcium Phosphate Cement Formulations to Widen Clinicl Applcation", Doctoral Thesis, University of Birmingham, 2012.*
Desai et al, "A Self Setting, Monetite (caHPO4) Cement for Skeletal Repair", Advances in Bioceramics and Biocomposites !!, 2007.*
Brown et al., "A new calcium phosphate setting cement," *J. Dental Res.* (1983) 62: 672. (IADR Abstracts 1983).
Getter et al., "Three biodegradable calcium phosphate slurry implants in bone," *Oral Surgery* (1972) 30: 263-268.
LeGeros et al., "Apatitic calcium phosphates: Possible dental restorative materials," *J. Dental Res.* (1982) 61: 343. (IADR Abstracts 1982).
Mosmann et al., "Rapid colorimetric assay for cellular growth and survival: Application to proliferation and cytotoxicity assays," *Journal of Immunological Methods* (1983) 65: 55-63.
Nakayama et al., "Assessment of the Alamar Blue assay for cellular growth and viability in vitro" *Journal of Immunological Methods* (1997) 204: 205-208.
Slater et al., "Studies on succinate-tetrazolium reductase systems III. Points of couping of four different teatrazolium salts," *Biochimica et Biophysica Acta* (1963) 77: 383-393.
Tamimi et al., "Bone augmentation in rabbit calvariae: comparative study between Bio-Oss® and a novel β-TCP/DCPD granulate," *J. Clin. Peridontol.* (2006) 33: 922-928.
Tamimi et al., "Bone regeneration in rabbit calvaria with novel monetite granules," *J. Biomed. Mater. Res.* (2008) 87A: 980-988.
Tamimi et al., "Bone regeneration in rabbit calvaria with novel monetite granules," *J. Biomed. Mater. Res.* (2007) 81A: 93-102.

* cited by examiner

*Primary Examiner* — Carlos Azpuru
(74) *Attorney, Agent, or Firm* — Merchant & Gould P.C.

(57) ABSTRACT

The present invention incorporates new materials for bone regeneration, methods for their manufacture, and application in traumatology surgery, maxillofacial surgery, dental surgery, orthognatic surgery, endodontics, ophthalmology, neurosurgery and/or osteoporotic processes, and other indications where bone regeneration is required. In particular, the present invention incorporates synthetic materials with a 20% to a 95%, preferably between 40% and 90% in mass of monetite [$Ca_{1-x}M_xHPO_4$, where $0 \leq x \leq 0.05$, and where M can be a divalent metallic ion], and which in their final composition incorporate between 5% and 80%, preferably between 0% and 60%, in mass of bioactive calcium compounds chosen from calcium phosphates and between 5% and 80% in total mass of bioactive silicon compounds chosen from calcium silicates and/or bioactive silica glasses and gels.

15 Claims, No Drawings

BONE REGENERATION MATERIALS BASED ON COMBINATIONS OF MONETITE AND OTHER BIOACTIVE CALCIUM AND SILICON COMPOUNDS

This application is a National Stage Application of PCT/EP2010/051386, filed 4 Feb. 2010, which claims benefit of International Application No. PCT/ES2009/070019, filed 10 Feb. 2009 and which applications are incorporated herein by reference. To the extent appropriate, a claim of priority is made to each of the above disclosed applications.

INVENTION FIELD

The invention relates to the field of biomaterials, more specifically to the field of calcium phosphate biomaterials that have a positive contribution to bone regeneration. The synthetic monetite based materials of the present invention are of application to multiple bone regeneration treatments in the medical and veterinary fields, in traumatology surgery, maxillofacial surgery, dental surgery, orthognatic surgery, endodontics, ophthalmology, neurosurgery and/or osteoporotic processes, and other indications where bone regeneration is required.

BACKGROUND

Loss of bone mass and bone quality is a serious health problem that can be more so in patients of advanced age. After intervention in odontology treatments there is often a loss of bone mass that results in complications and pathologies. This occurs, for example, in alveolar resorption following dental extraction and in periodontal disease. On the other hand, in traumatology and in other surgical interventions, loss of bone mass is a serious health problem that can even result in death of the patient.

For almost a century biomaterials have been used to repair or replace bone segments of the muscular-skeletal system. Autologous bone grafts, that is from the patient himself, are commonly used to fill bone cavities and in surgical reconstructions. However, there is a limited source of bone and these procedures subject patients to additional trauma to obtain the graft. Another option is that of donor allografts. However, these have a slower bone resorption and neoformation, reduced vascularisation and osteogenic capacity, and a greater immune response and risk of transmission of pathogens. An alternative are materials made from bovine bone, such as BioOss®, GenOx Inorg® and Orthoss®, which are commonly used in dentistry. However, the use of these products based on biological materials has problems of possible contamination with infectious agents and requires strict quality controls. With the aim of avoiding these problems synthetic matrices have been developed. Research into new synthetic biomaterials for bone repair has aimed at reducing to a minimum the requirement for bone grafts by means of an artificial equivalent that is reabsorbed in time and/or integrates adjacent bone, and also serves as a support for osteoporotic fractures. The mechanical properties of this artificial bone material should be as close to spongy bone as possible. The material must also contribute to the stability of the fracture and be sufficiently resistant to reduce the time in which immobilisation or external support is required. The replacement material must be biodegradable, biocompatible and osteoinductive, that is it should attract mesenchymal cells close to the implant and favour their differentiation into osteoblasts, and should also be osteoconductive, that is act as a guide for the formation of new bone.

Calcium phosphates have a special interest in bone regeneration because they resemble the mineral phase of natural bone and they are susceptible of bone remodelling and resorption. The most frequently used calcium phosphates include matrices of hydroxyapatite, tricalcium phosphate and brushite. These materials can be administered in the form of cementing pastes, implantable solids or granular or powder formulations.

In the development of bone regeneration matrices a special mention should be given to products which claim improved bone regeneration by means of incorporating a certain degree of porosity. The introduction of porosity in the system considerably increases the surface area of the material at the site of implant and the surface which is susceptible of interacting with cells of the surrounding tissues. Examples of porous hydroxyapatite of coral origin include Interpore® and ProOsteon®. Furthermore, examples of synthetic hydroxyapatite include Apafill-G® or ENGIpore®. Other commercial granular synthetic matrices of beta tricalcium phosphate include chronOs® and Cerasorb®. The latter is commercialised as particles with different sizes between 150 μm and 2000 μm depending on the need, and commonly used in alveolar regeneration after mixing with the patient's blood. Another similar product is Bi-Ostetic™, which is formed by particles between 1000 μm and 2000 μm composed by a mixture of hydroxyapatite and tricalcium phosphate. Furthermore, Collagraft® is another granular material based on hydroxyapatite and tricalcium phosphate which also incorporates collagen. Other synthetic osteoinductive materials incorporated in commercial products such as CalMatrix™ include calcium sulphate.

In the area of materials with growing interest in bone regeneration is dicalcium phosphate dihydrate $[CaHPO_4 \cdot 2H_2O]$, of mineralogic name "brushite", that can be found in nature or synthetically produced by means of acid-base reactions of calcium phosphates (LeGeros et al. 1982 J. Dental Res. 61:343; Brown W E y Chow L C. 1983 J. Dental Res. 62: 672). In the area of the use of brushite, there have been recent descriptions of combinations of brushite and tricalcium phosphate resulting from a manufacturing process with excess tricalcium phosphate. It has been shown that a granular material composed of 87% in mass of brushite and 17% in mass of beta-tricalcium phosphate is more degradable and results in greater bone formation than the commercial bovine hydroxyapatite BioOss® (Tamimi F. et al. 2006 J. Clin. Periodontol 33:922-928).

Dicalcium phosphate $[CaHPO_4]$, of mineralogic name "monetite", is a material considerably different from brushite which can be found as a mineral in nature, synthesised directly, or by a decomposition reaction of brushite. There are a few precedents in the use of monetite in bone regeneration, such as descriptions of the use of natural monetite mineral mixed with blood of the patient (Getter L, et al. 1972 J. Oral Surg. 30:263-268) or its incorporation into protein solutions (WO98/58602) or biodegradable polymers (US2005209704). More recently monetite has been evaluated in animal models of bone regeneration (Tamimi F. et al. 2008 J. Biomed. Mater. Res. 87A:980-988). However, the use of monetite in bone regeneration has not been exploited as it has been considered a material which is not optimum for bone regeneration because of its rapid dissolution and low mechanical strength. An example of this can be found in the formulation of brushite granules (Tamimi F. et al. 2007 J. Biomed. Mater. Res. 81A:93-102) were high temperatures that result in the conversion of brushite into monetite are intentionally avoided.

INVENTION SUMMARY

The present invention describes synthetic monetite matrices which are improved by means of the incorporation of other bioactive calcium compounds that modulate the degradation time of the resulting material, promote bone regeneration, and improve their osteoinductivity, osteoconductivity and biomechanical properties.

The present invention incorporates new materials for bone regeneration and repair, methods for their manufacture, and application in traumatology surgery, maxillofacial surgery, dental surgery, orthognatic surgery, endodontics, ophthalmology, neurosurgery and/or osteoporotic processes, and other indications where bone regeneration is required.

The materials are based on combinations of biocompatible, biodegradable, osteoconductive and osteoinductive elements. In particular, the present invention incorporates synthetic materials with 20% to 95%, preferably between 40% and 90% in total mass of monetite [$Ca_{1-x}M_xHPO_4$, where $0 \leq x \leq 0.05$, and where M can be a divalent metallic ion], and which in their final composition incorporate between 0% and 80%, preferably between 0% and 60%, in total mass of bioactive calcium compounds and between 5% and 80% in total mass of bioactive silicon compounds. The incorporation of these bioactive calcium and/or silicon compounds permits the modulation of the speed of degradation and the osteoconductivity, osteoinductivity and strength of monetite matrices. The bioactive calcium compounds include calcium phosphates, and the bioactive silicon compounds include calcium silicates, and/or bioactive silica glasses and gels. Furthermore, the materials of the present invention can incorporate pharmacological agents and/or biocompatible agents, and/or protective agents in solution, or as particles or granules that contribute favourably to bone regeneration, have a particular therapeutic activity, modulate the degradation time, or contribute to improved mechanical strength. These materials can be made from acid-base reactions which result in materials containing brushite, and other reaction products and remaining reactants. Conversion of the brushite fraction into monetite by means of heat treatment results in the desired materials. These materials can be manufactured in the form of powders, granules or monolith structures with a shape and size determined by a mould or by three-dimensional conformation methods, and their final shape can be modified by sculpture, erosion or pulverisation. The materials can be made to contain biocompatible agents and/or pharmacological agents that favour bone regeneration, and can be obtained with different mechanic resistance, degree of porosity, which can be interconnected or not, and different pore size.

DETAILED DESCRIPTION

The present invention incorporates new materials for bone regeneration, methods for their manufacture, and their application in animal and human health in traumatology surgery, maxillofacial surgery, dental surgery, orthognatic surgery, endodontics, ophthalmology, neurosurgery and/or osteoporotic processes, and other indications where bone regeneration is required. The materials are based on biocompatible, bioactive, biodegradable, osteoconductive and osteoinductive elements. In the present invention the materials described refer to the following chemical formula and definitions:

Monetite: mineralogic name for dicalcium phosphate [$CaHPO_4$], which also incorporates partially substituted monetite [$Ca_{1-x}M_xHPO_4$, where $0<x \leq 0.05$, and where M is divalent metallic ion such as Mg, Sr, Ba, Fe, Zn, among others].

Brushite: mineralogic name for dicalcium phosphate dihydrate [$CaHPO_4 \cdot 2H_2O$], which also incorporates partially substituted brushite [$Ca_{1-x}M_xHPO_4 \cdot 2H_2O$, donde $0<x \leq 0.05$, and where M is divalent metallic ion such as Mg, Sr, Ba, Fe, Zn, among others].

Monocalcium phosphate: [$Ca(H_2PO_4)_2$].

Monocalcium phosphate monohydrate [$Ca(H_2PO_4)_2 \cdot H_2O$].

Tricalcium phosphate [$Ca_3(PO_4)_2$] indistinctively any of its stable crystalline polymorphs, beta-tricalcium phosphate [$\beta$-$Ca_3(PO_4)_2$] or alpha-tricalcium phosphate [$\alpha$-$Ca_3(PO_4)_2$], and amorphous tricalcium phosphate.

Octacalcium phosphate [$Ca_8H_2(PO_4)_6 \cdot 5H_2O$].

Hydroxyapatites: Mineralogic name for the family of compounds with the chemical formula [$Ca_{10}(PO_4)_6(OH)_2$] where Ca can be partially replaced by Na, K, Sr, Mg, Zn, the $PO_4$ can be partially replaced by $HPO_4$, $CO_3$, $SiO_4$, and the OH can be partially replaced by F, Cl, $CO_3$. These can range from highly crystallised to hardly crystallized.

Wollastonite: calcium metasilicate [$CaSiO_3$], indistinctively alpha-wollastonite [$\alpha$-$CaSiO_3$] or beta-wollastonite [$\beta$-$CaSiO_3$].

Mixed calcium metasilicate: [$CaM(SiO_3)_2$] where M can be a metallic divalent ion such as Mg, Sr, Ba, Fe, Zn.

Calcium orthosilicate: [$Ca_2SiO_4$], indistinctively alpha-calcium orthosilicate [$\alpha$-$Ca_2SiO_4$], beta-calcium orthosilicate [$\beta$-$Ca_2SiO_4$], or gamma-calcium orthosilicate [$\gamma$-$Ca_2SiO_4$].

Tricalcium silicate: [$Ca_3SiO_5$].

Bioactive silica glasses: Vitreous materials, obtained either by fusion methods or by sol-gel, including in their composition Si and Ca, and that can also contain P, Na, Mg, Sr, among others, at concentrations such that a bioactive material can be obtained. Bioactive silica glasses include the systems $SiO_2$—$CaO$, $SiO_2$—$CaO$—$P_2O_5$, $SiO_2$—$CaO$—$ZnO$, $SiO_2$—$CaO$—$MgO$, $SiO_2$—$CaO$—$P_2O_5$—$ZnO$, and/or $SiO_2$—$CaO$—$P_2O_5$—$MgO$ Hydrated silica gel: [—$Si(OH)_2$—$O$—]$_n$.

In particular, the present invention incorporates synthetic materials that contain between 20% and 95%, preferably between 40% and 90%, in total mass of monetite [$Ca_{1-x}M_xHPO_4$, where $0 \leq x \leq 0.05$, and where M is a divalent metallic ion such as Mg, Sr, Ba, Fe, Zn, among others], and that in their final composition incorporate between 0% and 80%, preferably between 0% and 60%, in total mass of other bioactive calcium compounds and between 5% and 80% in total mass of bioactive silicon compounds. Monetite is an osteoconductive material that, due to its low mechanical strength and rapid dissolution in the organism or in biological media, does not make a good material for bone regeneration. The incorporation of bioactive calcium compounds into monetite matrices of the present invention allows for the modulation of the rate of degradation of the resulting materials and improves their osteoconductivity, osteoinductivity and biomechanical properties.

Obviously, the synthetic materials described in the present invention are not limited to these components and can comprise further components.

The "bioactive calcium compounds" incorporated in the monetite matrices include calcium phosphates other than monetite, among others, brushite, tricalcium phosphate, hydroxyapatites and octacalcium phosphate.

The "bioactive silicon compounds" include, among others, wollastonite, mixed calcium metasilicates, calcium orthosilicate, tricalcium silicate, and bioactive silica glasses and gels. Silica glasses include glasses, which can be obtained by fusion or sol-gel methods, which have in their composition Si and Ca, and can also contain P, Na, Mg, Sr, among others, at concentrations such that a bioactive material is obtained.

As is illustrated, without limitation, in Examples 1-13, these bioactive calcium compounds and bioactive silicon compounds can be incorporated into monetite matrices generated from heterogeneous acid-base reactions which result in brushite that is subsequently decomposed to monetite.

The first step in the synthesis of the materials of the present invention involves an acid-base reaction in which the acid component is a solution of orthophosphoric acid [$H_3PO_4$] or its monobasic salts of alkaline or alkaline earth metals, preferably of Ca or Mg, such as monobasic calcium phosphate or monobasic calcium phosphate monohydrate, and the basic components are solid bioactive calcium compounds and/or bioactive silicon compounds. Addition of an excess of the basic solid component to the reaction mixture results in a brushite matrix, as a product of the reaction, which contains the unreacted excess of bioactive calcium compounds and/or bioactive silicon compounds. The result of the acid-base reaction, with excess of the bioactive calcium compounds and/or bioactive silicon compounds acting as the basic components, originate solids containing between 24% and 96% in mass of brushite and between 4% and 76% in mass of the unreacted bioactive calcium compounds and/or bioactive silicon compounds depending on the initial formulation of the acid-base reaction. In the formulation of the acid-base reaction, the basic solid components generally have a particle size between 0.01 μm and 300 μm, preferably between 0.05 μm and 100 μm, and are present in a proportion liquid/solid between 0.4 ml/g and 3 ml/g, preferably between 0.8 ml/g and 2 ml/g. Mixing the acid-base reaction components originates a paste that rapidly solidifies, with the shape of the mould in which it is contained, as a result of the precipitation of the brushite product of the reaction. When one of the basic components in the reaction mixture is a wollastonite, a mixed calcium metasilicate, calcium orthosilicate, tricalcium silicate, and/or a bioactive silica glass, one of the products of the acid-base reaction, in addition to brushite, is a hydrated silica gel which embeds the resulting solid matrix.

In order to slow down the acid-base reaction and allow for a better manipulation of the paste, the aqueous solution preferably incorporates a retarding agent which includes, among others and without limitation, citric acid [$C_6H_8O_7$] or its alkaline or ammonia salts, sulphuric acid [$H_2SO_4$] or its alkaline, alkaline earth or ammonia salts, glycolic acid [$C_2H_4O_3$] or its alkaline or ammonia salts, acetic acid [$C_2H_4O_2$] or its alkaline or ammonia salts, and pyrophosphoric acid [$H_4P_2O_7$], or its alkaline or ammonia salts.

A second step in the synthesis of the materials of the present invention involves the decomposition of the brushite fraction into monetite by heat treatment at temperatures between 40° C. and 400° C., preferably between 40° C. and 200° C. This heat treatment can be carried out in a second step, or can be performed simultaneously to the formation of brushite resulting from the acid-base reaction. The decomposition of the brushite fraction results in the materials of the present invention, containing between 20% and 95%, preferably between 40% and 90%, in mass of monetite, and between 0% and 80%, preferably between 0% and 60%, in mass of bioactive calcium compounds and between 5% and 80% in total mass of bioactive silicon compounds.

As is illustrated, without limitation, in Examples 67 and 13, this synthesis method also permits the manufacture of monetite matrices that contain more than one bioactive calcium compound and/or bioactive silicon compound, such as brushite, tricalcium phosphate, octacalcium phosphate, hydroxyapatites, wollastonite and/or bioactive silica glasses and gels. Including more than one of these bioactive calcium compounds to the acid-base reaction, results in monetite matrices that in their final composition contain different proportions of these bioactive calcium compounds. The presence of between 5% and 80% of bioactive silica compounds represent a preferred realisation of this invention. These bioactive silica compounds include wollastonite, mixed calcium metasilicates, calcium orthosilicate, tricalcium silicates, and bioactive silica glasses and gels. The incorporation of these bioactive silica compounds results in materials with greater surface area and porosity, and higher cohesion and mechanical strength. The incorporation of bioactive silica compounds buffer the acid pH resulting from the dissolution and posterior conversion to apatite of monetite and other bioactive calcium compounds in the matrix providing matrices that are rapidly colonised by bone forming cells and result in a rapid and complete osteointergration.

Therefore, a preferred realization of the present invention incorporates synthetic materials containing between 20% and 95%, preferably between 40% and 90%, in total mass of monetite, and between 0% and 80%, preferably between 0% and 60% in total mass of other bioactive calcium compounds, and between 5% and 80% in total mass of bioactive silicon compounds, and their obtention by acid-base reactions of one or more basic reactants in excess and, when necessary, the transformation of the obtained brushite fraction into monetite.

As is illustrated, with out limitation, in Example 8, the monetite matrices of the present invention can incorporate substitutions with divalent metallic ions (M) such as magnesium, strontium, iron, or zinc, that stimulate bone regeneration or cellular colonization or differentiation. Incorporation of these substitutions in the monetite fraction can be carried out by incorporation of the metal ions to the reaction by addition of the corresponding monobasic phosphates such as $Mg(H_2PO_4)_2$, $Zn(H_2PO_4)_2$, $Sr(H_2PO_4)_2$, or precursors of these salts, such as the corresponding oxides, hydroxides, or carbonates y and the equivalent amount of orthophosphoric acid. The acid-base reaction of monocalcium phosphates with one or more basic calcium phosphates in excess, in the presence of metallic ions, results in the precipitation of partially substituted brushite or monetite. The subsequent decomposition of the partially substituted brushite results in partially substituted monetite matrices containing other bioactive calcium compounds and/or bioactive silicon compounds. The materials can be made with different proportions of monetite, partially substituted monetite, and other bioactive calcium compounds and/or bioactive silicon compounds. In one realisation of the present invention the partially substituted monetite can make up most of the final material. In one realisation of the present invention the atomic substitution of the calcium ions with the divalent ion within the monetite fraction is below 5%, and preferably between 2% and 4%, as expressed by formula [$Ca_{1-x}M_xHPO_4$], where $0 \leq x \leq 0.05$ and where M is a divalent metallic ion. These materials demonstrate improved osteoinductivity, osteoconductivity and significantly reduced biodegradation compared to non substituted monetite. Therefore, in a preferred embodiment of the present invention the monetite fraction is partially substituted with Mg, Zn, and/or Sr. An even more preferred embodiment of the present invention, illustrated with out limitation in Example 13, incorporates bioactive silicon compounds and monetite partially substituted with Mg, Zn, and/or Sr. These materials present significant advantages over unsubstituted materials and silicon-free materials regarding in vitro and in vivo biological bone regenerating capabilities and increased consistency and hardness.

As is illustrated, without limitation, in Examples 9 and 10, the materials of the present invention can incorporate "biocompatible agents" that modulate the biodegradation, favour bone formation, and/or increase resistance of the material, such as and with out limitation, albumin, hyaluronic acid, agarose, alginate, casein, collagen, celluloses, elastin, fibrin, gelatine, chitosan, silk, or of synthetic origin such as polylactic acid, polyglycolic acid, polyurethane, polypropylene, polycaprolactone, polyvinylpyrrolidone, polyvinyl alcohol, polyamides, polycarbonate, polytetrafluorethylene, and derivatives or mixtures thereof. Some of these biocompatible agents can be incorporated into the monetite matrices during their manufacture by means of their dissolution in the aqueous phase of the acid-base reaction, as is illustrated without limitation in Example 9. In this case, the agents in solution are homogeneously distributed in the monetite matrices, providing with greater strength and/or improvements in their capacity to regenerate bone and/or biodegradation. In one realisation of the present invention, the concentration of soluble materials is below 15%, preferably below 7%, and more so below 5% in mass of the materials containing monetite.

In another realisation of the present invention, the biocompatible agents are poorly soluble in aqueous media and are incorporated in the acid-base reaction in the form of suspensions, emulsions, precipitates, powders, granulates or fibres, as is illustrated, without limitation, in Example 10. In the case of the inclusion in the form of fibres, these can have diameters that can vary between 10 μm and 2000 μm, preferably between 50 μm and 1000 μm, and can make up to 70% in volume of the material containing monetite. Fibres rapidly dissolving in vivo favour the formation of interconnected pores and cellular colonisation of the material resulting from the invasion by osteoprogenitor cells.

The incorporation of these biocompatible agents does not only confer the monetite matrices with greater resistance but also improves the rheology of the paste and contributes to a greater capacity to regenerate bone. This is of special application in the manufacture of monoliths, either by three-dimensional conformation methods or by means of a mould with a shape and size according to the intended application and/or patient requirements.

The materials of the present invention can also be formulated to contain "pharmacological agents" that favour bone regeneration processes as is illustrated without limitation in Example 11. These pharmacological agents include, without limitation, synthetic or biological compounds or macromolecules that promote bone regeneration processes and/or have a therapeutic action. These pharmacological agents include antibiotics, anti-inflammatory and anti-tumour agents, bisphosphonates, nucleic acids, and cell growth factors such as platelet derived growth factor (PDGF), vascular endothelial growth factor (VEGF), bone morphogenetic protein (BMP), transforming growth factor-$\beta$ (TGF-$\beta$), growth hormone (GH), insulin like growth factor-1 (IGF1); insulin like growth factor-2 (IGF2), and/or fibroblast growth factor, FGF).

These pharmacological agents can be incorporated to the acid-base reaction either as powders or granules. More so, the aqueous phase of the acid-base reaction can contain stabilisers and/or protective agents to improve the stability of the bioactive agents, such as, and without limitation, trehalose, sucrose, raffinose, mannitol, polyvinyl alcohol, polyvinylpyrrolidone, albumin, collagen and/or gelatine. Addition of these stabilisers and/or protective agents avoids degradation of the pharmacological agent during the heat treatment for the conversion of brushite to monetite and provides long term stability. Alternatively, the pharmacological agents can be incorporated to the materials of the present invention by impregnation of the product resulting from the acid-base reaction, or impregnation of the final product after the heat treatment for the conversion of the brushite fraction into monetite. The incorporation of stabilising and/or protective agents avoids degradation of the pharmacological agents during the impregnation, heat treatment, drying and/or storage.

As is illustrated, without limitation, in Example 12, the materials containing monetite can be formulated with different degrees of porosity and pores of different sizes which can be isolated or communicated. This can be carried out by means of incorporating agents that result in the liberation of gas during the acid-base reaction and hardening of the paste. Examples of these pore inducing (porogenic) agents include, without restriction, calcium carbonate, calcium bicarbonate, sodium bicarbonate or hydrogen peroxide. The liberation of gas originates materials that after hardening have an induced porosity, which is in addition to the intrinsic porosity of the material, of up to 60% in volume, and with pore diameters that can vary between 1 μm and 1000 μm. Furthermore, the porosity of the materials can also be increased by incorporating additives to the acid-base reaction that after hardening of the mixture and their removal by dissolution result in the formation of pores. Examples of these additives include, without restriction, organic or inorganic salts, sugars, sugar alcohols, amino acids, proteins, polysaccharides or soluble polymers. More so, the materials of the present invention can be manufactured with a designed porosity by carrying out the acid-base reaction and hardening of the paste in a mould that once removed originates a defined macroporosity defined as pores or channels with a diameter over 200 μm.

The materials of the present invention can be manufactured as powders, granules, or in the form of monoliths with a shape, size and macroporosity predetermined by a mould. The reactants can also be incorporated into conformation systems, such as three-dimensional printing or extrusion, for the manufacture of three-dimensional monoliths with the desired shape, size and pore structure. Furthermore, after hardening of the paste as a result of the acid-base reaction, the shape and size of the resulting solid can be modified by fragmentation, abrasion, filing and/or pulverisation. This procedure can be carried out prior or after the conversion of the brushite fraction into monetite. The monoliths made from the materials of the present invention are of application to surgical interventions in which it is necessary to reconstruct or fuse a bone mass with a given shape and size.

In another preferred realisation of the present invention, the material is produced in the form of granules. Granule size can be between 50 μm and 4000 μm, preferably, granule size is between 200 μm and 2000 μm. This granular form is of special interest in alveolar reconstruction and other indications where it is necessary to have new bone formed within a cavity.

The materials containing monetite and other bioactive calcium compounds and/or bioactive silicon compounds described in the present invention are biocompatible, biodegradable, osteoinductive, and osteoconductive, and have a special interest and application in the manufacture of materials with medical and veterinary applications, in traumatology surgery, maxillofacial surgery, dental surgery, orthognatic surgery, endodontics, ophthalmology, neurosurgery and/or osteoporotic processes. Furthermore, as is illustrated in Example 5, the materials of the present invention are useful for in vitro culture of autologous cells that when implanted into the patient together with the materials of the present invention accelerate the bone regeneration process.

The present invention is further illustrated by the following 13 Examples that are meant to be illustrative and are not intended to be limitative in their scope.

EXAMPLES

Example 1

Monetite and Tricalcium Phosphate Material

To obtain a material made of monetite and tricalcium phosphate $[Ca_3(PO_4)_2]$, the different amounts of reactants, alpha- or beta-tricalcium phosphate and monocalcium phosphate $[Ca(H_2PO_4)_2]$, shown in Table 1 are thoroughly mixed. To the mixture of powders 2.0 mL of a 0.8 M solution of citric acid are added. The resulting paste is mixed rapidly for 1 min and is then left to set for 24 h in a chamber at 100% relative humidity and a temperature of 50-60° C. in order to complete the acid-base reaction and decompose the brushite formed into monetite. The hardened pastes are dried at 100-110° C. and are crushed and classified with sieves to collect fractions with the desired particle size. The final phase composition of the obtained granules is determined by X-ray diffraction (qualitative) and thermogravimetric analysis (quantitative) and is shown in Table 1.

TABLE 1

| Amount of reactants | | | Final phase composition | |
|---|---|---|---|---|
| $Ca_3(PO_4)_2$ (g) | $Ca(H_2PO_4)_2$ (g) | Citric A. 0.8M (mL) | % mass $CaHPO_4$ | % mass $Ca_3(PO_4)_2$ |
| (β) 1.26 | 0.96 | 2.0 | 96% | (β) 4% |
| (β) 1.42 | 0.80 | 2.0 | 82% | (β) 18% |
| (β) 1.62 | 0.60 | 2.0 | 63% | (β) 37% |
| (β) 1.74 | 0.48 | 2.0 | 41% | (β) 59% |
| (α) 1.42 | 0.80 | 2.0 | 84% | (α) 16% |
| (α) 1.74 | 0.48 | 2.0 | 43% | (α) 57% |

Example 2

Monetite and Octacalcium Phosphate Material

To obtain a material composed of 80-85% in mass of monetite and 15-20% in mass of octacalcium phosphate $[Ca_8H_2(PO_4)_6 \cdot 5H_2O]$, 0.60 g of monocalcium phosphate and 1.62 g of octacalcium phosphate are thoroughly mixed. To the mixture of powders 2.0 mL of a 0.8 M solution of citric acid are added. The resulting paste is mixed rapidly for 1 min and is then left to set for 24 h in a chamber at 100% relative humidity and a temperature of 50-60° C. in order to complete the acid-base reaction and decompose the brushite formed into monetite. The hardened paste is air dried and crushed and classified with sieves to collect fractions with the desired particle size. The obtained granulate is sterilised with a dose of a 25 kGy gamma radiation.

Example 3

Monetite and Hydroxyapatite Material

To obtain a material composed of 80-85% in mass of monetite and 15-20% in mass of hydroxyapatite $[Ca_{10}(PO_4)_6(OH)_2]$, 0.88 g of monocalcium phosphate and 1.34 g of hydroxyapatite are thoroughly mixed. To the mixture of powders 2.0 mL of a 0.8 M solution of citric acid are added. The resulting paste is mixed rapidly for 1 min and is then left to set for 24 h in a chamber at 100% relative humidity and a temperature of 50-60° C. in order to complete the acid-base reaction and decompose the brushite formed into monetite. The hardened paste is air dried and crushed and classified with sieves to collect fractions with the desired particle size. The obtained granulate is sterilised with a dose of a 25 kGy gamma radiation.

Example 4

Solubility of Different Monetite Materials Containing Bioactive Calcium Compounds To determine the dissolution rate of monetite matrices containing different proportions of monetite and different bioactive calcium compounds, 100 mg of each material, previously ground to a particle size below 100 μm are placed in vials. To each vial 100 mL of a buffered solution pH 6.0 (100 mM $KCOOCH_3$; adjusted with KOH and/or $HCOOCH_3$) are added. The vials are stoppered and placed in an orbital shaker at 36.5° C. for 30 min. The supernatants were then filtered through a Teflon membrane (0.45 μm) and the calcium (Ca) concentration in the filtrate is determined by Inductively Coupled Plasma Atomic Emission Spectrophotometry. Three replicas are carried out per material. The average concentration of dissolved Ca for each material after incubation in the buffered solution is shown in Table 2. For each of the different calcium phosphates, the amount of dissolved Ca from the granules, and therefore the solubility of the material, depends directly on the ratio monetite/calcium phosphate. For materials containing different calcium phosphates within the monetite matrices, the solubility depends on the type of calcium phosphate in the following order: octacalcium phosphate>alpha-tricalcium phosphate>beta-tricalcium phosphate>hydroxyapatite.

TABLE 2

| Final phase composition | | Ca dissolved in 30 min |
|---|---|---|
| % mass $CaHPO_4$ | % mass Calcium Phosphate | (mg/L) |
| 96% | 4% β-$Ca_3(PO_4)_2$ | 98 ± 1 |
| 82% | 18% β-$Ca_3(PO_4)_2$ | 85 ± 1 |
| 63% | 37% β-$Ca_3(PO_4)_2$ | 70 ± 2 |
| 41% | 59% β-$Ca_3(PO_4)_2$ | 62 ± 2 |
| 84% | 16% α-$Ca_3(PO_4)_2$ | 90 ± 1 |
| 81% | 19% $Ca_{10}(PO_4)_6(OH)_2$ | 78 ± 2 |
| 60% | 40% $Ca_{10}(PO_4)_6(OH)_2$ | 64 ± 2 |
| 81% | 19% $Ca_8H_2(PO_4)_6 \cdot 5H_2O$ | 96 ± 1 |
| 65% | 35% $Ca_8H_2(PO_4)_6 \cdot 5H_2O$ | 93 ± 1 |

Example 5

Cell Colonisation and Bone Regeneration of Monetite Materials Containing Bioactive Calcium Compounds To determine the bone regeneration capacity of different monetite matrices containing bioactive calcium compounds, the matrices are incubated in the presence of rabbit bone marrow stem cells. Briefly, bone marrow cells are recollected and suspended in 10 mL of Earls Minimum Essential Medium with glutamine and non-essential amino acids and supplemented with 1 mM sodium pyruvate, 1.5 g/L sodium bicarbonate, 60 mg/ml kanamycin sulphate and 15% foetal bovine serum. A suspension of $10^5$ cells is added to wells containing 0.5 g of the test material in the form of granules between 200 μm and 2000 μm in diameter. Cellular colonisation of the material is determined after 7 days incubation by the MTT indirect staining method (according to Mosman T 1983 J. Immunol. Meth. 65: 55-63). Furthermore, to determine the bone forming capacity the different materials were implanted in a rabbit model with a 1 cm diameter orifice in their skull. The evaluation of the material is carried out six weeks after implant following sacrifice and autopsy of the animal. One of the cell populated materials is also implanted in the bone regeneration model. Table 3 shows the data of the cell colonisation model and the in vivo evaluation of the different monetite matrices containing bioactive calcium compounds. The effects observed can be classified as "Very Abundant: +++++", "Abundant: ++++", "Moderate: +++", "Scarce: ++", "None: +". The incorporation of the bioactive calcium compounds results in an improvement in the capacity to support cell growth and bone regeneration capacity.

TABLE 3

| Final phase composition | | Cell growth [determined by MTT] | Bone regeneration [in vivo evaluation] |
|---|---|---|---|
| $CaHPO_4$ (% mass) | Calcium phosphate (% mass) | | |
| 98% | 2% $\beta$-$Ca_3(PO_4)_2$ | ++ | ++ |
| 82% | 18% $\beta$-$Ca_3(PO_4)_2$ | ++++ | ++++ |
| 82% | 18% $\beta$-$Ca_3(PO_4)_2$ + cells | Not determined | +++++ |
| 63% | 37% $\beta$-$Ca_3(PO_4)_2$ | ++++ | ++++ |
| 41% | 59% $\beta$-$Ca_3(PO_4)_2$ | +++ | +++ |
| 84% | 16% $\alpha$-$Ca_3(PO_4)_2$ | ++ | +++ |
| 0% | 100% $\beta$-$Ca_3(PO_4)_2$ | ++ | ++ |
| 81% | 19% $Ca_{10}(PO_4)_6(OH)_2$ | ++++ | +++ |
| 60% | 40% $Ca_{10}(PO_4)_6(OH)_2$ | ++++ | +++ |
| 0% | 100% $Ca_{10}(PO_4)_6(OH)_2$ | ++ | ++ |
| 81% | 19% $Ca_8H_2(PO_4)_6 \cdot 5H_2O$ | ++++ | +++ |
| 0% | 100% $Ca_8H_2(PO_4)_6 \cdot 5H_2O$ | ++ | + |

Example 6

Monetite, Wollastonite and Hydrated Silica Gel Material with or without Beta-Tricalcium Phosphate To obtain a material composed of 38-43% in mass of monetite, 34-39% in mass of alpha—wollastonite [$\alpha$-$CaSiO_3$] and 21-26% in mass of hydrated silica gel [—$Si(OH)_2$—O—]$_n$, 2.66 mL of an aqueous solution of orthophosphoric acid (3.5 M) and citric acid (0.8 M) are added to 2.22 g of alpha-wollastonite with a particle size smaller than 50 μm. The components are mixed thoroughly for 1 minute to obtain a paste. Alternatively, to obtain a material with 38-43% in mass of monetite, 33-38% in mass of beta-tricalcium phosphate, 0-2% in mass of alpha-wollastonite, and 21-26% in mass of hydrated amorphous silica gel, 2.66 mL of an aqueous solution of orthophosphoric acid (3.5 M) and citric acid (0.8 M) are added to a mixture containing 1.11 g of alpha- or beta-wollastonite and 1.11 g of beta-tricalcium phosphate, both as powders with particle size smaller than 50 μm. The components are mixed thoroughly for 1 minute to obtain a paste.

The pastes resulting from the different compositions are poured into silicone moulds in the shape of 20 mm diameter and 5 mm deep discs. The disc shapes obtained after hardening of the paste are left for 24 h in a chamber at 20-30° C. and 100% relative humidity to complete the acid-base reaction. The discs are dried in an oven at 100-110° C. to decompose the brushite into monetite and eliminate the water absorbed by the silica gel. The phase composition of the solids obtained is determined by X-ray diffraction and thermal analysis as shown in Table 4.

The in vitro bioactivity of the materials obtained is compared with that of a material with the same disc shape composed by 40% in mass of monetite and 60% in mass of beta-tricalcium phosphate. For this, discs are incubated for different time periods in simulated physiological fluid (pH 7.3 a 36.5° C.) and the time recorded for the first signs, and the total coverage, of the surface with globular apatite (according to Kokubo and Takadama 2006 Biomaterials 27:2907-29). The incorporation of alpha-wollastonite and hydrated silica gel to the monetite matrices results in an increase in the in vitro bioactivity of the resulting materials as shown in Table 4.

TABLE 4

| Phase Composition of the Material (% in Mass) | First signs of coverage | Total coverage |
|---|---|---|
| 40% Monetite/ 37% beta-tricalcium phosphate/ 23% hydrated silica gel | 6 h | 24 h |
| 40% Monetite/ 36% beta-tricalcium phosphate/ 1% beta-wollastonite/ 23% hydrated silica gel | 12 h | 48 h |
| 40% Monetite/ 60% beta-tricalcium phosphate | 48 h | 96 h |

Example 7

Monetite, Bioactive Glass, and Hydrated Silica Gel Material with or without Beta-Tricalcium Phosphate To obtain a material composed of 41-45% in mass of monetite, 26-30% of bioactive glass of composition 70$SiO_2$-30CaO and 27-31% of hydrated silica gel [—$Si(OH)_2$—O—]$_n$, 1.54 g of bioactive glass with a particle size below 100 μm, and 0.96 g of monocalcium phosphate are mixed. To this mixture of powders, 2.71 mL of an aqueous solution of 1.0 M glycolic acid are added and mixed thoroughly for 1 minute to obtain a paste.

Alternatively, to obtain a material composed of 41-45% in mass of monetite, 12-16% of beta-tricalcium phosphate, 12-16% bioactive glass, and 27-31% of hydrated amorphous silica gel, 1.27 g of bioactive glass of composition 70$SiO_2$-30CaO and a particle size smaller than 100 μm, 0.40 g of beta-tricalcium phosphate with a particle size smaller than 100 μm, and 1.04 g of monocalcium phosphate are mixed. To the mixture of powders 2.71 mL of an aqueous solution of 0.8 M citric acid are added and mixed thoroughly for 1 minute to obtain a paste.

The resulting pastes are poured into silicone moulds in the shape of 20 mm diameter and 5 mm deep discs. The filled moulds are left for 48 h in a chamber at 50-60° C. and 100% relative humidity to complete the acid-base reaction and decompose the obtained brushite into monetite. The hardened discs are removed from the moulds and dried in an oven at 100-110° C. to eliminate the water absorbed by the silica gel. The solids obtained are characterised by X-ray diffraction and thermal analysis. The discs obtained from both materials are incubated for different time periods in simulated physiological fluid (pH 7.3 a 36.5° C.) and the time recorded for the first signs, and the total coverage, of the surface with globular apatite (according to Kokubo and Takadama 2006 Biomaterials 27:2907-29). As is shown in Table 5, the in vitro bioactivity is greater for materials containing bioactive glasses.

TABLE 5

| Phase composition of the material (% in mass) | First signs of coverage | Total coverage |
| --- | --- | --- |
| 43% Monetite/ 28% bioactive glass/ 29% silica gel | 3 h | 24 h |
| 43% Monetite/ 14% beta-tricalcium phosphate/ 14% bioactive glass/ 29% silica gel | 3 h | 24 h |
| 100% Monetite | 96 h | 120 h |

Example 8

Monetite Material Partially Substituted with Metallic Ions and Tricalcium Phosphate To obtain materials composed by 80-85% in mass of monetite partially substituted with magnesium or by zinc, and by 15-20% in mass of beta-tricalcium phosphate, 0.68 g of monocalcium phosphate and 1.54 g of beta-tricalcium phosphate with particle size below 100 μm are intimately mixed. To this mixture of powders, 2.0 mL of a 1.0 M glycolic acid solution and 0.4 M $Mg(H_2PO_4)_2$ or $Zn(H_2PO_4)_2$ are added. The resulting paste is mixed thoroughly for 1 minute and poured into silicone moulds in the shape of 15 mm diameter and 3 mm deep discs to obtain discs with these dimensions. The discs are left for 24 h in a chamber at 50-60° C. and 100% relative humidity to complete the acid-base reaction and decompose the produced brushite into monetite. The discs are removed from the moulds and left to air dry. The resulting materials, according to X-ray diffraction analysis, thermogravimetric analysis, scanning electron microscopy and microanalysis by x-ray energy dispersive spectroscopy, are composed by 80-85% in mass of monetite partially substituted by magnesium or by zinc, and 15-20% in mass of beta-tricalcium phosphate. The substitution of Ca by Mg and Zn in the monetite reticulum, according to microanalysis of granules of this phase, result in a 4% atomic substitution of Ca by Mg and a 3% atomic substitution of Ca by Zn respectively.

The capacity of the materials substituted with Zn or with Mg to promote cellular adhesion is determined by Alamar Blue assay (according to Nakayama et al. 1997 J. Immunol. Methods 204:205-208). Briefly, disks are sterilised with gamma radiation (25 kGy) and four discs of each of the materials (substituted with Zn or with Mg, or with no substitution), or four Thermanox™ discs of equal diameter (as a control), are placed in the wells of 24 well plates. To each well 1 mL of a $1.4 \times 10^5$ cells/mL suspension in complete MEM (Minimum Essential Medium) of a primary human fibroblast cell culture is added. Plates are incubated at 37±1° C. for one day and the media removed together with those cells that still remain in suspension. To the wells containing the discs and adhered cells, 1 mL of a solution of Alamar Blue (dilution 1:10 of Alamar Blue, Serotec, BUFO12A, with MEM without phenol red) is added and the plates are incubated for 4 h at 37±1° C. For each reading point an empty blank is included by replacing the cell suspension with 1 mL of the Alamar Blue solution. From each well 4 aliquots of 100 μL are transferred to wells of a 96 well plate to determine the optical density at 570 nm with a reference wave length of 630 nm. The wells containing the materials and the adhered cells are washed with a phosphate buffered saline solution and 1 mL of complete MEM is added to continue the incubation at 37±1° C. until the next reading time point. Readings are carried out on days 1, 4, 7, 14, and 21. The optical density measured is directly proportional to the number of viable cells adhered on the surface of the tested materials. Table 6 shows the optical density readings for each sample and incubation period. The three tested materials showed an initial cellular adhesion of 60% compared to Thermanox™, and considerable proliferation during the incubation time. For all the time periods the greatest cell numbers were found associated to the material substituted with Mg, followed by the material substitutes with Zn, and to a lesser extent the un-substituted material.

TABLE 6

| | Optical density for each incubation time (days) | | | | |
| --- | --- | --- | --- | --- | --- |
| Material | 1 | 4 | 7 | 14 | 21 |
| Un-substituted | 0.178(0.008) | 0.307(0.010) | 0.290(0.019) | 0.330(0.017) | 0.315(0.018) |
| with Mg | 0.222(0.009) | 0.361(0.016) | 0.387(0.020) | 0.393(0.012) | 0.401(0.020) |
| with Zn | 0.197(0.011) | 0.324(0.019) | 0.346(0.021) | 0.366(0.014) | 0.387(0.015) |
| Thermanox ™ | 0.281(0.016) | 0.468(0.018) | 0.459(0.025) | 0.410(0.016) | 0.451(0.016) |

Example 9

Material Containing Biocompatible Agents Incorporated in Solution

To obtain materials that incorporate different soluble biocompatible agents, Type I collagen, sodium hyaluronate, or chitosan are dissolved at concentrations of 0.5% in mass in a 0.8 M solution of citric acid. To these solutions different proportions of monocalcium phosphate $[Ca(H_2PO_4)_2]$ with beta-tricalcium phosphate $[\beta\text{-}Ca_3(PO_4)_2]$, hydroxyapatite $[Ca_{10}(PO_4)_6(OH)_2]$ or diopside $[CaMg(SiO_3)_2]$, are added. The resulting pastes are mixed thoroughly for 1 min and placed in silicone moulds 5 mm diameter and 12 mm deep, or 15 mm diameter and 3 mm deep, to make cylinders and discs of these dimensions. The cylinders and discs are left for 24 h in a chamber at 20-30° C. and 100% relative humidity to complete the acid-base reaction. The discs are left to air dry and are removed from the silicone moulds. To obtain the final materials, the brushite fraction of the obtained materials is transformed into monetite by dry heat treatment at 60° C. for 2 hours.

The compression strength is determined on the 5 mm diameter cylinders on a biaxial Instron™ 8511 device. The tests are carried out at room temperature and at a speed of 1 mm/min until failure of the sample.

Determination of the capacity to sustain cell growth is carried out by cell culture of the osteoblast-like HOS cell line (ECACC no. 87070202) on the 15 mm diameter discs and observation of cell colonisation by microscopy and MTT reduction assay (according to Mosman T 1983 J. Immunol. Meth. 65: 55-63; y Slater T. F. et al. 1963 Biochim. Biophys. Acta 77:383-93). Observations were carried out at different times for 7 days.

Determination of the capacity to regenerate bone is carried by implant in artificial bone defects in rat tibia and subsequent histological evaluation of the bone segments containing the sites of implant after sacrifice of the animals at 7, 30 and 120 days. The materials for implantation are obtained from the fragments resulting from the resistance to compression assay after crushing into granules with a size between 200 μm and 2000 μm and sterilisation with gamma radiation (25 kGy).

The obtained materials, their compression strength, capacity to sustain cell growth, and capacity to regenerate bone in an animal model are shown in Table 7. Incorporation of these biocompatible agents to monetite matrices results in an improvement in their capacity to sustain cell growth and regenerate bone. The effects observed can be classified as "Very Abundant: +++++", "Abundant: ++++", "Moderate: +++", "Scarce: ++", "None: +".

TABLE 7

| % in mass Inorganic components | % in mass Biocompatible agents | Strength (MPa) | Adhesion and cell proliferation | Bone regeneration |
|---|---|---|---|---|
| $CaHPO_4$ 95-100% | No additive | 4 ± 1 | ++ | ++ |
| $CaHPO_4/\beta\text{-}Ca_3(PO_4)_2$ 80-85%/20-15% | No additive | 7 ± 1 | ++ | +++ |
| $CaHPO_4/\beta\text{-}Ca_3(PO_4)_2$ 80-85%/20-15% | 0.5% Hyaluronate | 11 ± 2 | ++++ | ++++ |
| $CaHPO_4/\beta\text{-}Ca_3(PO_4)_2$ 80-85%/20-15% | 0.5% Collagen | 10 ± 1 | ++++ | ++++ |
| $CaHPO_4/\beta\text{-}Ca_3(PO_4)_2$ 65-70%/35-30% | 0.5% Chitosan | 9 ± 2 | +++ | +++ |
| $CaHPO_4/Ca_{10}(PO_4)_6(OH)_2$ 80-85%/20-15% | No additive | 6 ± 1 | ++ | +++ |
| $CaHPO_4/Ca_{10}(PO_4)_6(OH)_2$ 80-85%/20-15% | 0.5% Hyaluronate | 8 ± 1 | ++++ | ++++ |
| $CaHPO_4/Ca_{10}(PO_4)_6(OH)_2$ 65-70%/35-30% | 0.5% Collagen | 7 ± 1 | ++++ | ++++ |
| $CaHPO_4/Ca_{10}(PO_4)_6(OH)_2$ 80-85%/20-15% | 0.5% Chitosan | 7 ± 1 | +++ | +++ |
| $Ca_{0.97}Mg_{0.03}HPO_4/CaMg(SiO_3)_2/$ Silica gel 80-85%/15-13%/5-2% | No additive | 5 ± 2 | +++ | ++++ |
| $Ca_{0.97}Mg_{0.03}HPO_4/CaMg(SiO_3)_2/$ Silica gel 80-85%/15-13%/5-2% | 0.5% Hyaluronate | 7 ± 2 | ++++ | ++++ |
| $Ca_{0.97}Mg_{0.03}HPO_4/CaMg(SiO_3)_2/$ Silica gel 65-70%/32-29%/3-1% | 0.5% Collagen | 6 ± 1 | +++++ | +++++ |
| $Ca_{0.97}Mg_{0.03}HPO_4/CaMg(SiO_3)_2/$ Silica gel 80-85%/15-13%/5-2% | 0.5% Chitosan | 7 ± 1 | ++++ | ++++ |

Example 10

Monoliths Containing Monetite and Fibres of Biocompatible Agents

To obtain materials incorporating different organic biocompatible agents as fibres, different fibres were manufactured from type I collagen or alternatively from polylactide-polyglycolic (50:50), by means of electro-spinning techniques from aqueous solutions for collagen and from a dimethylformamide solution for the polylactide-polyglycolic. The fibres have a final diameter between 10 μm and 1000 μm depending on the parameters used in their manufacture. The fibres are intimately mixed with 1.55 g of monocalcium phosphate $[Ca(H_2PO_4)_2]$ and, 1.45 g of alpha-wollastonite $[\alpha\text{-}CaSiO_3]$ or alternatively 1.46 g of bioactive glass of composition $70SiO_2\text{-}30CaO$ (mol %), and 0.30 g of beta-tricalcium phosphate $[\beta\text{-}Ca_3(PO_2)_2]$, and to the mixtures 3.0 mL and 1.9 mL, respectively, of a 0.8 M citric acid solution is added. The resulting pastes are thoroughly mixed for 1 min and poured into silicone moulds to the shape of a bone and left for 24 h in a chamber at 100% relative humidity and a temperature of 20-30° C. Once hardened, the different materials are left to air dry. To obtain the final products, the brushite fraction of the materials is transformed into monetite by heat treatment at 100° C. for 2 hours. The resulting materials contain 55-65% in mass of monetite, 15-30% in mass of silica gel and 22-33% of alpha-wollastonite or 9-12% of bioactive glass $(70SiO_2\text{-}30CaO)$, and approximately 20% in volume of Type I collagen or polylactide-polyglycolic fibres. The incorporation of the fibres results in greater mechanical resistance and favours cellular colonisation.

Example 11

Monetite and Beta-Tricalcium Phosphate Materials with Antibiotic

To obtain monetite and beta-tricalcium phosphate materials with antibiotics, 2.11 g of beta-tricalcium phosphate with a particle size bellow 100 μm, 0.11 g of sodium ceftriaxone, and 25 mg of trehalose are thoroughly mixed. To the mixture, 1.53 mL of a 2.0 M orthophosphoric acid solution are added and the resulting paste is mixed thoroughly for 1 minute and compacted into 15 mm diameter and 3 mm depth silicone moulds to make discs of these dimensions. The discs are left in the moulds for 24 h in a chamber with 100% relative humidity and a temperature of 50-60° C. to complete the acid-base reaction and decompose the formed brushite into monetite. Discs are removed from the moulds and sterilised with gamma rays.

To study the liberation of the antibiotic discs are placed in vials. To half of the discs a pH 7.4 phosphate buffer is added (8 mM $K_2HPO_4$, 2 mM $KH_2PO_4$, 2.7 mM KCl, 137 mM NaCl) and to the other half a pH 4.0 phosphate buffer is added (1 mM $KH_2PO_4$, 137 mM NaCl, 2.7 M KCl), at a volumetric solid/liquid ratio of 1:10. Vials are placed on an orbital shaker set at 37° C. during the 15 days of the study. The determination of the amount of ceftriaxone released to the medium is carried out by UV spectroscopy and comparison with a standard curve. During the first seven hours of the study the determinations are carried out every hour, for the second to the fourth day every 24 h, and in the remaining period every 3 days at the most. For each determination all the liquid is removed and replaced with fresh buffer. The release profiles of ceftriaxone at pH 4.0 and 7.4 are shown in Table 8.

TABLE 8

| Time | Ceftriaxone accumulated, mg/L | |
|---|---|---|
| (Hours) | pH 4.0 | pH 7.0 |
| 1.4 | 714 | 706 |
| 2.8 | 970 | 1014 |
| 3.7 | 1007 | 1091 |

TABLE 8-continued

| Time (Hours) | Ceftriaxone accumulated, mg/L | |
|---|---|---|
| | pH 4.0 | pH 7.0 |
| 5.5 | 1064 | 1194 |
| 6.4 | 1112 | 1246 |
| 24.8 | 1275 | 1477 |
| 49.2 | 1388 | 1698 |
| 73.6 | 1494 | 1904 |
| 144.8 | 1633 | 2336 |
| 216.0 | 1778 | 2778 |
| 312.6 | 1909 | 2953 |

Example 12

Monoliths with Collagen and Induced Porosity

To obtain materials with 80-85% in mass of monetite, 15-20% in mass of beta-tricalcium phosphate, 0.45% in mass of collagen, and different degrees of induced porosity, a 0.1% to 3% in mass of calcium carbonate is added as a pore forming (porogeninc) agent to a mixture of 1.42 g beta-tricalcium phosphate and 0.80 g de monocalcium phosphate. To the mixture of powders 2.0 mL of a 0.8 M citric acid solution containing 0.5% mass/vol. of collagen Type I are added. The resulting paste is mixed thoroughly for 1 minute, poured into a 3 mm diameter and 6 mm deep cylindrical mould and left to set for 12 hours in a chamber with 100% relative humidity and a temperature of 20-30° C. Once hardened the different materials are left to air dry. To obtain the final products, the brushite fraction of the obtained materials is transformed into monetite by thermal treatment at 45° C. for 2 hours. The resulting materials show an induced porosity, in addition to the natural microporosity of the material, up to 50% and a pore size between 50 μm y 800 μm. Evaluation of the capacity of the resulting materials to sustain cell growth is carried out by cell culture for 7 days of the osteoblast-like cell line HOS (ECACC no. 87070202), microscopic observation of cell colonisation and MTT reduction assay (according to Mosman T 1983 J. Immunol. Meth. 65: 55-63; y Slater T. F. et al. 1963 Biochim. Biophys. Acta 77:383-93). Observations are carried out at different times for 7 days.

Furthermore, the efficacy of the obtained materials in bone regeneration is evaluated in artificial bone defects in rat tibia. For this 90 healthy rats (Rattus norvegicus, Holtzman, ~200 g) are used. Groups of 30 animals are used for each time point (7, 30 and 120 days). Three animals from each group received bilateral implants of the same experimental material in 3 mm defects created in the mid section (diaphysis) of the tibia. In three animals from each group the artificial defects were left empty as controls. Animals are sacrificed by lethal injection with thiopental after 7, 30 and 120 days, and the bone segments containing the control and implant sites are recovered. The bone segments are fixed in Bouin solution, washed, decalcified, dehydrated and embedded in paraffin. Serial 6 μm thickness sections are cut and stained with haematoxylin and eosin for histological examination. The degree of new bone formation is evaluated and classified as "Very Abundant: +++++", "Abundant: ++++", "Moderate: +++", "Scarce: ++", "None: +". The materials obtained, their capacity to sustain cell proliferation and the evaluation of their capacity to regenerate bone in a rat animal model are shown in Table 9. The incorporation of porosity to the materials results in an increased capacity to support cell proliferation and regenerate bone.

TABLE 9

| Materials % in mass Monetite/% Tricalcium phosphate | % in volume of Induced Porosity | Cellular adhesion, extension & proliferation | Bone regeneration |
|---|---|---|---|
| 100% | 0% | ++ | ++ |
| 80-85%/20-15% | 0% | +++ | +++ |
| 65-70%/35-30% | 0% | +++ | +++ |
| 80-85%/20-15% | 10% | ++++ | ++++ |
| 65-70%/35-30% | 10% | ++++ | ++++ |
| 80-85%/20-15% | 20% | ++++ | ++++ |
| 65-70%/35-30% | 20% | ++++ | +++ |
| 80-85%/20-15% | 30% | ++++ | ++++ |
| 65-70%/35-30% | 50% | ++++ | +++ |

Example 13

Monetite Materials, Substituted or not with Mg, Zn and Sr, Containing Bioactive Silicon Compounds and/or Bioactive Calcium Compounds To determine the beneficial effect of the incorporation of bioactive silicon compounds, different monetite matrices, substituted or not with Mg, Zn and Sr listed in Table 10, were produced and compared with matrices without bioactive silicon compounds with regard to their in vivo behaviour. Briefly, the monetite matrices were obtained by reaction between a basic component consisting of beta-tricalcium phosphate and/or alpha-wollastonite and/or bioactive glass of composition $70SiO_2$-$30CaO$, with an acid solution of phosphoric acid in stoichiometric or short amount. For the synthesis of monetites substituted with Zn or Mg ions, the necessary amounts of $2ZnCO_3.3Zn(OH)_2$, $4MgCO_3.Mg(OH)_2$ or $SrCO_3$ respectively were dissolved in the phosphoric acid solution. A liquid/powder rate between 0.8 and 1.2 was used. After the addition of the liquid to the powder, the resulting paste was mixed thoroughly for 30 seconds and left to set for 24 hours in a chamber with 100% relative humidity at 60° C. Once hardened the different materials were dried at 60° C. The materials were manually grinded and sieved. The fraction of granules between 250 μm and 1000 μm were used for the in vivo assay. Previous to their implantation materials were sterilized at 121° C. and 1 atm. of overpressure for 20 minutes.

For the in vivo assay the granules were implanted in bones of sheep. Six 13 mm-deep by 8 mm-diameter holes were drilled in the right and left humeral, tibia and femur of all sheep. A total of 12 sheep were used. Each experimental material is randomly implanted in six bone defects and six randomly selected holes left empty and used as control. Bone regeneration and resorption of the implanted materials in every defect is evaluated by X-ray, nuclear magnetic resonance, and histological examination 12 weeks after of implantation. The degree of new bone formation, bone regeneration, is evaluated and classified as "Very Abundant: +++++", "Abundant: ++++", "Moderate: +++", "Scarce: ++", "None: +" and shown in Table 10. The incorporation of silicon compounds to the monetite containing matrices of the present invention, and especially in those in which the monetite is partially substituted with Mg, Zn or Sr has a clear beneficial effect in bone regeneration.

To determine the consistence of the formed granules and to certain extent their hardness, 2 g of granules ranging between 250 and 1000 microns in diameter are put inside polyethylene bottles containing a rubber ball. Bottles are shaken in an orbital shaker for 30 minutes and the materials obtained sieved to determine the fraction of particles smaller than 250 microns. Materials with the highest proportion of remaining particles larger than 250 microns are considered to have grater consistence and hardness. The degree of consistence, and indirectly hardness, of the materials is classified as "Very Consistent: +++++", "Consistent: ++++", "Moderately Consistent: +++", "Soft: ++", "Very Soft: +" and shown in Table 10. The incorporation of Silicon Compounds and partial substitution of the monetite matrix with Mg, Zn or Sr ions is shown to have a positive contribution on the consistence and hardness of the resulting materials.

TABLE 10

Final Phase Composition

| $Ca_{1-x}M_xHPO_4$ | | | % mass of Calcium Phosphate | Bioactive Calcium and Silicon Compounds | Granule Consistence | Bone Regener. |
|---|---|---|---|---|---|---|
| % mass | M | x | | % mass of Silicon Compound | | |
| 100% | — | 0 | — | — | ++ | ++ |
| 80% | — | 0 | 20% $\beta\text{-}Ca_3(PO_4)_2$ | — | + | +++ |
| 80% | — | 0 | 14.4% $\beta\text{-}Ca_3(PO_4)_2$ | 5.6% Silica gel | +++ | ++++ |
| 80% | Zn | 0.03 | 20% $\beta\text{-}Ca_3(PO_4)_2$ | — | +++ | +++ |
| 60% | — | — | — | 5.6% $\alpha\text{-}CaSiO_3$ 34.4% Silica gel | +++++ | +++++ |
| 60% | Mg | 0.03 | — | 5.6% $\alpha\text{-}CaSiO_3$ 3.4% Silica gel | +++++ | ++++ |
| 60% | Mg | 0.03 | 7% $\beta\text{-}Ca_3(PO_4)_2$ | 33% Silica Gel | ++++ | +++++ |
| 60% | Mg | 0.03 | 7% $Ca_{10}(PO_4)_6(OH)$ | 33% Silica Gel | ++++ | +++++ |
| 60% | — | — | — | 10% Glass 70S30C 30% Silica gel | ++++ | ++++ |
| 60% | Mg | 0.03 | — | 10% Glass 70S30C 30% Silica gel | ++++ | +++++ |
| 60% | Sr | 0.03 | — | 10% Glass 70S30C 30% Silica Gel | +++++ | +++++ |
| EMPTY HOLES | — | — | — | — | - | + |

The invention claimed is:

1. A synthetic bone regeneration material, the synthetic material comprising:
   a. 20% to 95% in total mass of monetite [$Ca_{1-x}M_xHPO_4$], where $0 \leq x \leq 0.05$ and M is a divalent metallic ion;
   b. between 5% and 80% in total mass of bioactive silicon compounds selected from wollastonite, mixed calcium metasilicates, calcium orthosilicate, tricalcium silicate, and bioactive silica glasses and gels and/or combinations thereof;
   c. between 0% and 60% in total mass of bioactive calcium phosphates selected from brushite, monocalcium phosphate, monocalcium phosphate monohydrate, tricalcium phosphates, octacalcium phosphates, hydroxyapatites, and combinations thereof; and
   d. optionally, biocompatible agents, pharmacological agents, and/or protective agents.

2. The synthetic material according to claim 1, where "x" is equal to zero.

3. The synthetic material according to claim 1, where the divalent metallic ion (M) is magnesium, strontium, barium, iron, and/or zinc.

4. The synthetic material according to claim 1, where the calcium phosphate is a hydroxyapatite [$Ca_{10}(PO_4)_6(OH)_2$], where the calcium is partially replaced by sodium, potassium, strontium, magnesium and/or zinc; the phosphate is partially replaced by hydrogenphosphate, carbonate, silicate; and/or the hydroxyl is partially replaced by fluorine, chlorine or carbonate.

5. The synthetic material according to claim 1, where the bioactive silicon compound is alpha-wollastonite and/or beta-wollastonite [$\alpha$- or $\beta\text{-}CaSiO_3$].

6. The synthetic material according to claim 1, where the bioactive silicon compound is a calcium silicate [$CaM(SiO_3)_2$] which contains a divalent metallic ion (M) selected from magnesium, strontium, barium, iron and/or zinc.

7. The synthetic material according to claim 1, where a bioactive calcium silicon compound is a bioactive glass in the systems $SiO_2$—$CaO$, $SiO_2$—$CaO$—$P_2O_5$, $SiO_2$—$CaO$—$ZnO$, $SiO_2$—$CaO$—$MgO$, $SiO_2$—$CaO$—$P_2O_5$—$ZnO$, and/or $SiO_2$—$CaO$—$P_2O_5$—$MgO$.

8. The synthetic material according to claim 1, where a bioactive silicon compound is a silica gel.

9. The synthetic material according to claim 1, that incorporate biocompatible agents in their composition.

10. The synthetic material according to claim 1, that incorporates pharmacological agents in their composition.

11. The synthetic material according to claim 1, in the form of granules between 50 μm and 4000 μm.

12. The synthetic material according to claim 1, in the shape of three-dimensional monoliths with the shape and size determined by a bone defect.

13. A method for obtaining the synthetic bone regeneration material according to claim 1, comprising:
   a. Performing an acid-base reaction in an aqueous media to form brushite, in which the acid component is orthophosphoric acid or its monobasic salts of alkaline or alkaline earth metals, and the basic component is constituted by one or more bioactive silicon compounds, and optionally by bioactive calcium compounds, which are present in excess; and
   b. Decomposing the brushite obtained from the acid-base reaction by thermal treatment into monetite.

14. A composition comprising the synthetic bone regeneration material according to claim 1, wherein the synthetic material comprises animal or human cells.

15. A method for bone regeneration comprising implanting the synthetic bone regeneration material according to claim 1 into a patient in need thereof.

* * * * *